(12) United States Patent
Rothe

(10) Patent No.: US 7,595,161 B2
(45) Date of Patent: Sep. 29, 2009

(54) EFFICACY OF CALCIMIMETIC AGENTS

(76) Inventor: Hansjoerg Martin Rothe, Eselerstrasse 32, Nordlingen (DE) D-86720

(*) Notice: Subject to any disclaimer, the term of this patent is extended or adjusted under 35 U.S.C. 154(b) by 405 days.

(21) Appl. No.: 11/456,712

(22) Filed: Jul. 11, 2006

(65) Prior Publication Data

US 2007/0105134 A1 May 10, 2007

Related U.S. Application Data

(60) Provisional application No. 60/735,608, filed on Nov. 10, 2005.

(51) Int. Cl.
| | | |
|---|---|---|
| C12Q 1/68 | (2006.01) | |
| C12P 19/34 | (2006.01) | |
| C07H 21/02 | (2006.01) | |
| C07H 21/04 | (2006.01) | |

(52) U.S. Cl. .................. 435/6; 435/91.1; 435/91.2; 536/24.3

(58) Field of Classification Search .................. None
See application file for complete search history.

(56) References Cited

U.S. PATENT DOCUMENTS

| | | | |
|---|---|---|---|
| 5,435,972 A | 7/1995 | Daw et al. | |
| 5,688,938 A | 11/1997 | Brown | |
| 5,763,569 A | 6/1998 | Brown | |
| 5,858,684 A | 1/1999 | Nemeth | |
| 5,967,314 A | 10/1999 | McGovern | |
| 6,011,068 A | 1/2000 | Nemeth | |
| 6,031,003 A | 2/2000 | Nemeth et al. | |
| 6,211,244 B1 | 4/2001 | Van Wagenen et al. | |
| 6,313,146 B1 | 11/2001 | Van Wagenen et al. | |

OTHER PUBLICATIONS

Rothe et al; Pharmacogenetics and genomics, vol. 15, Jan. 2005, pp. 29-34.*

Urena et al; Kidney International, vol. 63, Supplement 85, pp. S91-S96, 2003.*

Hegele (Arterioscler. Thromb. Vasc. Biol.; 2002, vol. 22, pp. 156-1061.*

Lucentini (The Scientist; 2004, vol. 24, p. 20.*

Juppner; Bone, vol. 17; 1995, pp. 39S-40S.*

Rothe, HM., et al., "Calcium-sensing Receptor Gene Polymorphism ARG$^{990}$ Gly and its Possible Effect on Response to Cinacalcet HCl," Pharmacogenetics Genomics. Jan. 2005; 15(1):29-34.

Rothe, HM, et al., "Calcium-sensing receptor gene polymorphism Arg$^{990}$Gly influences the response to a single dose of cinacalcet HCl." JASN 16, 66A, Abstract No. F-FC128 (Nov. 10, 2005).

(Continued)

*Primary Examiner*—Jehanne S Sitton
(74) *Attorney, Agent, or Firm*—Scott E. Kamholz; Foley Hoag LLP

(57) ABSTRACT

A method of assessing the efficacy of a calcimimetic drug to treat hyperparathyroidism in a subject may include determining which alleles for a calcium-sensitive receptor (CaSR) gene the subject carries; and concluding that the calcimimetic drug will have a first or highest efficacy if the subject has a $^{990}$Gly-$^{990}$Gly genotype, a second or intermediate efficacy if the subject has a $^{990}$Gly-$^{990}$Arg genotype, or a third or lowest efficacy if the subject has a $^{990}$Arg-$^{990}$Arg genotype. In one embodiment, the calcimimetic drug may be cinacalcet or any pharmaceutically acceptable salt thereof.

9 Claims, 7 Drawing Sheets

OTHER PUBLICATIONS

Rothe, HM, et al., "Calcium-sensing receptor gene polymorphism Arg$^{990}$Gly influences the severity of secondary hyperparathyroidism in hemodialysis patients." JASN 16, 752A, Abstract No. SA-PO895 (Nov. 10, 2005).

* cited by examiner

FIG. 7A: CaSR-$^{930}$Gly cDNA Sequence

```
caacaggcacctggctgcagccaggaaggaccgcacgcccctttcgcgcaggagagtggaaggagggagctgtttgccagcaccg
aggtcttgcggcacaggcaacgcttgacctgagtcttgcagaatgaaaggcatcacaggaggcctctgcatgatgtggcttcca
aagactcaaggaccacccacattacaagtctggattgaggaaggcagaaatggagattcaaacaccacgtcttctattatttta
ttaatcaatctgtagacatgtgtcccactgcagggagtgaactgctccaagggagaaacttctgggagcctccaaactcctag
ctgtctcatcccttgccctggagagacggcagaaccatggcattttatagctgctgctggtcctcttggcactcacctggcac
acctctgcctacgggccagaccagcgagcccaaaagaaggggggacattatccttgggggctctttcctattcattttggagta
gcagctaaagatcaagatctcaaatcaaggccggagtctgtggaatgtatcaggtataatttccgtgggtttcgctggttacag
gctatgatatttgccatagaggagataaacagcagcccagcccttcttcccaacttgacgctgggatacaggatatttgacact
tgcaacaccgtttctaaggccttggaagccaccctgagttttgttgctcaaaacaaaattgattctttgaaccttgatgagttc
tgcaactgctcagagcacattccctctacgattgctgtggtgggagcaactggctcaggcgtctccacggcagtggcaaatctg
ctggggctcttctacattccccaggtcagttatgcctcctcagcagactcctcagcaacaagaatcaattcaagtctttcctc
cgaaccatccccaatgatgagcaccaggccactgccatggcagacatcatcgagtatttccgctggaactgggtgggcacaatt
gcagctgatgacgactatgggcggccggggattgagaaattccgagaggaagctgaggaaagggatatctgcatcgacttcagt
gaactcatctcccagtactctgatgaggaagagatccagcatgtggtagaggtgattcaaaattccacggccaaagtcatcgtg
gttttctccagtggcccagatcttgagcccctcatcaaggagattgtccggcgcaatatcacgggcaagatctggctggccagc
gaggcctgggccagctcctccctgatcgccatgcctcagtacttccacgtggttggcggcaccattggattcgctctgaaggct
gggcagatcccaggcttccgggaattcctgaagaaggtccatcccaggaagtctgtccacaatggttttgccaaggagttttgg
gaagaaacatttaactgccacctccaagaaggtgcaaaaggacctttacctgtggacacctttctgagaggtcacgaagaaagt
ggcgacaggtttagcaacagctcgacagccttccgaccctctgtacaggggatgagaacatcagcagtgtcgagaccccttac
atagattacacgcatttacggatatcctacaatgtgtacttagcagtctactccattgcccacgccttgcaagatatatatacc
tgcttacctgggagagggctcttcaccaatggctcctgtgcagacatcaagaaagttgaggcgtggcaggtcctgaagcaccta
cggcatctaaactttacaaacaatatggggggcaggtgacctttgatgagtgtggtgaccggtggggaactattccatcatc
aactggcacctctccccagaggatggctccatcgtgtttaaggaagtcgggtattacaacgtctatgccaagaaggagaaaga
ctcttcatcaacgaggagaaaatcctgtggagtgggttctccagggaggtgcccttctccaactgcagccgagactgcctggca
gggaccaggaaagggatcattgaggggggagcccacctgctgctttgagtgtgtggagtgtcctgatggggagtatagtgatgag
acagatgccagtgcctgtaacaagtgcccagatgacttctggtccaatgagaaccacacctcctgcattgccaaggagatcgag
tttctgtcgtggacggagcccctttgggatcgcactcaccctctttgccgtgctgggcattttcctgacagcctttgtgctgggt
gtgtttatcaagttccgcaacacacccattgtcaaggccaccaaccgagagctctcctacctcctcctcttctccctgctctgc
tgcttctccagctccctgttcttcatcggggagcccaggactggacgtgccgcctgcgccagccggcctttggcatcagcttc
gtgctctgcatctcatgcatcctggtgaaaaccaaccgtgtcctcctggtgtttgaggccaagatccccaccagcttccaccgc
aagtggtggggcctcaacctgcagttcctgctggttttcctctgcacctttcatgcagattgtcatctgtgtgatctggctctac
accgcgccccctcaagctaccgcaaccaggagctggaggatgagatcatcttcatcacgtgccacagggcctccctcatggcc
ctgggcttcctgatcggctacacctgcctgctggctgccatctgcttcttctttgccttcaagtcccggaagctgccggagaac
ttcaatgaagccaagttcatcaccttcagcatgctcatcttcttcatcgtctggatctccttcattccagcctatgccagcacc
tatggcaagtttgtctctgccgtagaggtgattgccatcctggcagccagctttggcttgctggcgtgcatcttcttcaacaag
atctacatcattctcttcaagccatcccgcaacaccatcgaggaggtgcgttgcagcaccgcagctcacgctttcaaggtggct
gcccgggccacgctgcgccgcagcaacgtctcccgcaagcggtccagcagccttggaggctccacgggatccacccctcctcc
tccatcagcagcaagagcaacagcgaagaccccattcccacagcccgagaggcagaagcagcagcagccgctggccctaacccag
caagagcagcagcagccccctgaccctcccacagcagcaacgatctcagcagcagcccagatgcaagcagaaggtcatcttt
ggcagcggcacggtcacctctcactgagctttgatgagcctcagaagaacgccatggccacgggaattctacgcaccagaac
tccctggaggcccagaaaagcagcgatacgctgacccgacaccagccattactccgctgcagtgcggggaaacggacttagat
ctgaccgtccaggaaacaggtctgcaaggacctgtgggtggagaccagcggccagaggtggaggaccctgaagagttgtcccca
gcacttgtagtgtccagttcacagagctttgtcatcagtggtggaggcagcactgttacagaaaacgtagtgaattcataaaat
ggaaggagaagactggctagggagaatgcagagaggtttcttggggtcccagggatgaggaatcgcccagactcctttcctc
tgaggaagaagggataatagacacatcaaatgccccgaatttagtcacaccatcttaaatgacagtgaattgacccatgttccc
ttt
```

FIG. 7B: CaSR-$^{390}$Gly Protein Sequence

MAFYSCCWVLLALTWHTSAYGPDQRAQKKGDIILGGLFPIHFGV
AAKDQDLKSRPESVECIRYNFRGFRWLQAMIFAIEEINSSPALLPNLTLGYRIFDTCN
TVSKALEATLSFVAQNKIDSLNLDEFCNCSEHIPSTIAVVGATGSGVSTAVANLLGLF
YIPQVSYASSSRLLSNKNQFKSFLRTIPNDEHQATAMADIIEYFRWNWVGTIAADDDY
GRPGIEKFREEAEERDICIDFSELISQYSDEEEIQHVVEVIQNSTAKVIVVFSSGPDL
EPLIKEIVRRNITGKIWLASEAWASSSLIAMPQYFHVVGGTIGFALKAGQIPGFREFL
KKVHPRKSVHNGFAKEFWEETFNCHLQEGAKGPLPVDTFLRGHEESGDRFSNSSTAFR
PLCTGDENISSVETPYIDYTHLRISYNVYLAVYSIAHALQDIYTCLPGRGLFTNGSCA
DIKKVEAWQVLKHLRHLNFTNNMGEQVTFDECGDLVGNYSIINWHLSPEDGSIVFKEV
GYYNVYAKKGERLFINEEKILWSGFSREVPFSNCSRDCLAGTRKGIIEGEPTCCFECV
ECPDGEYSDETDASACNKCPDDFWSNENHTSCIAKEIEFLSWTEPFGIALTLFAVLGI
FLTAFVLGVFIKFRNTPIVKATNRELSYLLLFSLLCCFSSSLFFIGEPQDWTCRLRQP
AFGISFVLCISCILVKTNRVLLVFEAKIPTSFHRKWWGLNLQFLLVFLCTFMQIVICV
IWLYTAPPSSYRNQELEDEIIFITCHEGSLMALGFLIGYTCLLAAICFFFAFKSRKLP
ENFNEAKFITFSMLIFFIVWISFIPAYASTYGKFVSAVEVIAILAASFGLLACIFFNK
IYIILFKPSRNTIEEVRCSTAAHAFKVAARATLRRSNVSRKRSSSLGGSTGSTPSSSI
SSKSNSEDPFPQPERQKQQQPLALTQQEQQQQPLTLPQQQRSQQQPRCKQKVIFGSGT
VTFSLSFDEPQKNAMAH[G]NSTHQNSLEAQKSSDTLTRHQPLLPLQCGETDLDLTVQET
GLQGPVGGDQRPEVEDPEELSPALVVSSSQSFVISGGGSTVTENVVNS

FIG. 8A: CaSR-$^{990}$Arg cDNA Sequence caacaggcacctggctgcagccaggaaggaccgcacgcccttcgcgcaggagagtggaaggagggagctgtttgccagcaccgaggtcttg
cggcacaggcaacgcttgacctgagtcttgcagaatgaaaggcatcacaggaggcctctgcatgatgtggcttccaaagactcaaggaccac
ccacattacaagtctggattgaggaaggcagaaatggagattcaaacaccacgtcttctattattttattaatcaatctgtagacatgtgtc
cccactgcagggagtgaactgctccaagggagaaacttctgggagcctccaaactcctagctgtctcatcccttgccctggagagacggcag
aaccatggcattttatagctgctgctgggtcctcttggcactcacctggcacacctctgcctacgggccagaccagcgagcccaaaagaagg
gggacattatccttgggggctctttcctattcattttggagtagcagctaaagatcaagatctcaaatcaaggccggagtctgtggaatgt
atcaggtataatttccgtgggtttcgctggttacaggctatgatatttgccatagaggagataaacagcagcccagcccttcttcccaactt
gacgctgggatacaggatatttgacacttgcaacaccgtttctaaggccttggaagccaccctgagttttgttgctcaaaacaaaattgatt
ctttgaaccttgatgagttctgcaactgctcagagcacattccctacgattgctgtggtgggagcaactggctcaggcgtctccacggca
gtggcaaatctgctggggctcttctacattccccaggtcagttatgcctcctcagcagactcctcagcaacaagaatcaattcaagtctt
cctccgaaccatccccaatgatgagcaccaggccactgccatgcagacatcatcgagtatttccgctggaactgggtgggcacaattgcag
ctgatgacgactatgggcggccggggattgagaaattccgagaggaagctgaggaaagggatatctgcatcgacttcagtgaactcatctcc
cagtactctgatgaggaagagatccagcatgtggtagaggtgattcaaaattccacggccaaagtcatcgtggttttctccagtggcccaga
tcttgagcccctcatcaaggagattgtccggcgcaatatcacgggcaagatctggctggccagcgaggcctgggccagctcctccctgatcg
ccatgcctcagtacttccacgtggttgcggcaccattggattcgctctgaaggctgggcagatcccaggcttccgggaattcctgaagaag
gtccatcccaggaagtctgtccacaatggtttttgccaaggagttttgggaagaaacatttaactgccacctccaagaaggtgcaaaaggacc
tttacctgtggacaccttctgagaggtcacgaagaaagtggcgacaggtttagcaacagctcgacagccttccgaccctctgtacaggg
atgagaacatcagcagtgtcgagaccccttacatagattacacgcatttacggatatcctacaatgtgtacttagcagtctactccattgcc
cacgccttgcaagatatatatacctgcttacctgggagagggctcttccaccaatggctcctgtgcagacatcaagaaagttgaggcgtggca
ggtcctgaagcacctacggcatctaaactttacaaacaatatggggggaggggcaggtgaccttttgatgagtgtggtgacctggtggggaactatt
ccatcatcaactggcacctctccccagaggatggctccatcgtgttaaggaagtcgggtattacaacgtctatgccaagaaggagaaaga
ctcttcatcaacgaggagaaaatcctgtggagtgggttctccaggaggtgccttctccaactgcagccgagactgcctggcagggaccag
gaaagggatcattgagggggagcccacctgctgctttgagtgtgtggagtgtcctgatggggagtatagtgatgagacagatgccagtgcct
gtaacaagtgcccagatgacttctggtccaatgagaaccacacctcctgcattgccaaggagatcgagtttctgtcgtggacggagcccttt
gggatcgcactcaccctctttgccgtgctgggcattttcctgacagcctttgtgctgggtgtgtttatcaagttccgcaacacacccattgt
caaggccaccaaccgagagctctcctacctcctcctcttctccctgctctgctgcttctccagctccctgttcttcatcggggagccccagg
actggacgtgccgcctgcgccagccggcctttggcatcagcttcgtgctctgcatctcatgcatcctggtgaaaaccaaccgtgtcctcctg
gtgtttgaggccaagatccccaccagctctccaccgcaagtggtgggggctcaacctgcagttcctgctggttttcctctgcaccttcatgca
gattgtcatctgtgtgatctggctctacaccgcgcccctcaagtaccgcaaccaggagctggaggatgagatcatcttcatcacgtgcc
acgagggctccctcatggccctgggcttcctgatcggctacacctgcctgctggctgccatctgcttcttctttgccttcaagtcccggaag
ctgccggagaacttcaatgaagccaagttcatcaccttcagcatgctcatcttcttcatcgtctggatctccttcattccagcctatgccag
cacctatggcaagtttgtctctgccgtagaggtgattgccatcctggcagccagctttggcttgctggcgtgcatcttcttcaacaagatct
acatcattctcttcaagccatcccgcaacaccatcgaggaggtgcgttgcagcaccgcagctcacgctttcaaggtggctgcccgggccacg
ctgcgcgcagcaacgtctcccgcaagcggtccagcagccttggaggctccacgggatccaccccctcctcctccatcagcagcaagagcaa
cagcgaagacccatcccacagcccgagaggcagaagcagcagcagccgctggccctaacccagcaagagcagcagcagcagccctgaccc
tcccacagcagcaacgatctcagcagcagccagatgcaagcagaaggtcatctttggcagcggcacggtcaccttctcactgagctttgat
gagcctcagaagaacgccatggcccacaggaattctacgcaccagaacctccctggaggcccagaaaagcagcgatacgctgacccgacacca
gccattactcccgctgcagtgcggggaaacggacttagatctgaccgtccaggaaacaggtctgcaaggacctgtgggtggagaccagcggc
cagaggtggaggaccctgaagagttgtccccagcacttgtagtgtccagttcacagagctttgtcatcagtggtggaggcagcactgttaca
gaaaacgtagtgaattcataaaatggaaggagaagactgggctagggagaatgcagagaggtttcttggggtcccagggatgaggaatcgcc
ccagactcctttcctctgaggaagaagggataatagacacatcaaatgccccgaatttagtcacaccatcttaaatgacagtgaattgaccc
atgttccctttaaaattaaaaaaagaagagccttgtgtttctgtggttgcatttgtcaaagcattgagatctccacggtcagatttgctgt
tcacccacatctaatgtctcttcctctgttctatcccacccaacagctcagagatgaaactatggctttaaactaccctccagagtgtgcag
actgatgggacatcaaatttgccaccactagagctgagagtctgaaagacagaatgtcaccagtcctgcccaatgccttgacaacagactga
attttaaatgttcacaacataaggagaatgtatctcctcctatttatgaaaaccatatgatattttgtctcctacctgctgctgctattatg
taacatccagaaggtttgcaccctcctataccatatgtctgcttctgtccaggacatgatactgatgccatgtttagattccaggatcaca
agaatcacctcaaattgttaggaagggactgcataaaccaatgagctgtatctgtaattaatattcctatatgtagctttatccttaggaaa
atgcttctgttgtaatagtccatggacaatataaactgaaaaatgtcagtctggtttatataaggcagtattattgagctctatttccccac
cccactatcctcactcccataagctaagcctatgtgagcccttcagggactcaaggtccagaagtccctcccatctctaccccaaagaa
ttcctgaagccagatccaccctatccctgtacagagtaagttctcaattattggctgctaatagctgctagggtaggaaagcgtggttcca
agaaagatccaccctcaaatgtcagagctatgttccctccagcagtggtattaatactgccggtcacccaggctctggagccagagagacag
accggggttcaagccatggcttcgtcatttgcaagctgagtgactgtaggcagggaaccttaacctctctaagccacagcttcttcatcttt
aaaataaggataataatcattccttcccctcagagctcttatgtggattaaacgagataatgtatataaagtactttagcctggtacctagc
acacaataagcattcaataaatattagttaatattat FIG. 8B: CaSR-$^{990}$Arg Protein Sequence MAFYSCCWVLLALTWHTSAYGPDQRAQKKGDIILGGLFPIHFGV
AAKDQDLKSRPESVECIRYNFRGFRWLQAMIFAIEEINSSPALLPNLTLGYRIFDTCN
TVSKALEATLSFVAQNKIDSLNLDEFCNCSEHIPSTIAVVGATGSGVSTAVANLLGLF
YIPQVSYASSSRLLSNKNQFKSFLRTIPNDEHQATAMADIIEYFRWNWVGTIAADDDY
GRPGIEKFREEAEERDICIDFSELISQYSDEEEIQHVVEVIQNSTAKVIVVFSSGPDL
EPLIKEIVRRNITGKIWLASEAWASSSLIAMPQYFHVVGGTIGFALKAGQIPGFREFL
KKVHPRKSVHNGFAKEFWEETFNCHLQEGAKGPLPVDTFLRGHEESGDRFSNSSTAFR
PLCTGDENISSVETPYIDYTHLRISYNVYLAVYSIAHALQDIYTCLPGRGLFTNGSCA
DIKKVEAWQVLKHLRHLNFTNNMGEQVTFDECGDLVGNYSIINWHLSPEDGSIVFKEV
GYYNVYAKKGERLFINEEKILWSGFSREVPFSNCSRDCLAGTRKGIIEGEPTCCFECV
ECPDGEYSDETDASACNKCPDDFWSNENHTSCIAKEIEFLSWTEPFGIALTLFAVLGI
FLTAFVLGVFIKFRNTPIVKATNRELSYLLLFSLLCCFSSSLFFIGEPQDWTCRLRQP
AFGISFVLCISCILVKTNRVLLVFEAKIPTSFHRKWWGLNLQFLLVFLCTFMQIVICV
IWLYTAPPSSYRNQELEDEIIFITCHEGSLMALGFLIGYTCLLAAICFFFAFKSRKLP
ENFNEAKFITFSMLIFFIVWISFIPAYASTYGKFVSAVEVIAILAASFGLLACIFFNK
IYIILFKPSRNTIEEVRCSTAAHAFKVAARATLRRSNVSRKRSSSLGGSTGSTPSSSI
SSKSNSEDPFPQPERQKQQQPLALTQQEQQQQPLTLPQQQRSQQQPRCKQKVIFGSGT
VTFSLSFDEPQKNAMAHRNSTHQNSLEAQKSSDTLTRHQPLLPLQCGETDLDLTVQET
GLQGPVGGDQRPEVEDPEELSPALVVSSSQSFVISGGGSTVTENVVNS

SEQUENCE LISTING

<160> NUMBER OF SEQ ID NOS: 6

<210> SEQ ID NO 1
<211> LENGTH: 4913
<212> TYPE: DNA
<213> ORGANISM: Homo sapiens

<400> SEQUENCE: 1

| | | | | | |
|---|---|---|---|---|---|
| caacaggcac | ctggctgcag | ccaggaagga | ccgcacgccc | tttcgcgcag | gagagtggaa | 60 |
| ggagggagct | gtttgccagc | accgaggtct | tgcggcacag | gcaacgcttg | acctgagtct | 120 |
| tgcagaatga | aaggcatcac | aggaggcctc | tgcatgatgt | ggcttccaaa | gactcaagga | 180 |
| ccacccacat | tacaagtctg | gattgaggaa | ggcagaaatg | gagattcaaa | caccacgtct | 240 |
| tctattattt | tattaatcaa | tctgtagaca | tgtgtcccca | ctgcagggag | tgaactgctc | 300 |
| caagggagaa | acttctggga | gcctccaaac | tcctagctgt | ctcatcccttt | gccctggaga | 360 |
| gacggcagaa | ccatggcatt | ttatagctgc | tgctgggtcc | tcttggcact | cacctggcac | 420 |
| acctctgcct | acgggccaga | ccagcgagcc | caaaagaagg | gggacattat | ccttgggggg | 480 |
| ctctttccta | ttcattttgg | agtagcagct | aaagatcaag | atctcaaatc | aaggccggag | 540 |
| tctgtggaat | gtatcaggta | taatttccgt | gggtttcgct | ggttacaggc | tatgatattt | 600 |
| gccatagagg | agataaacag | cagcccagcc | cttcttccca | acttgacgct | gggatacagg | 660 |
| atatttgaca | cttgcaacac | cgtttctaag | gccttggaag | ccaccctgag | ttttgttgct | 720 |
| caaaacaaaa | ttgattcttt | gaaccttgat | gagttctgca | actgctcaga | gcacattccc | 780 |
| tctacgattg | ctgtggtggg | agcaactggc | tcaggcgtct | ccacgcagt | ggcaaatctg | 840 |
| ctggggctct | tctacattcc | ccaggtcagt | tatgcctcct | ccagcagact | cctcagcaac | 900 |
| aagaatcaat | tcaagtcttt | cctccgaacc | atccccaatg | atgagcacca | ggccactgcc | 960 |
| atggcagaca | tcatcgagta | tttccgctgg | aactgggtgg | gcacaattgc | agctgatgac | 1020 |
| gactatgggc | ggccggggat | tgagaaattc | cgagaggaag | ctgaggaaag | ggatatctgc | 1080 |
| atcgacttca | gtgaactcat | ctcccagtac | tctgatgagg | aagagatcca | gcatgtggta | 1140 |
| gaggtgattc | aaaattccac | ggccaaagtc | atcgtggttt | tctccagtgg | cccagatctt | 1200 |
| gagcccctca | tcaaggagat | tgtccggcgc | aatatcacgg | gcaagatctg | gctggccagc | 1260 |
| gaggcctggg | ccagctcctc | cctgatcgcc | atgcctcagt | acttccacgt | ggttggcggc | 1320 |
| accattggat | tcgctctgaa | ggctgggcag | atcccaggct | tccgggaatt | cctgaagaag | 1380 |
| gtccatccca | ggaagtctgt | ccacaatggt | tttgccaagg | agtttttggga | agaaacattt | 1440 |

-continued

```
aactgccacc tccaagaagg tgcaaaagga cctttacctg tggacacctt tctgagaggt   1500
cacgaagaaa gtggcgacag gtttagcaac agctcgacag ccttccgacc cctctgtaca   1560
ggggatgaga acatcagcag tgtcgagacc ccttacatag attacacgca tttacggata   1620
tcctacaatg tgtacttagc agtctactcc attgcccacg ccttgcaaga tatatatacc   1680
tgcttacctg ggagagggct cttcaccaat ggctcctgtg cagacatcaa gaaagttgag   1740
gcgtggcagg tcctgaagca cctacggcat ctaaacttta caaacaatat ggggagcag   1800
gtgacctttg atgagtgtgg tgacctggtg ggaactatt ccatcatcaa ctggcacctc   1860
tccccagagg atggctccat cgtgtttaag gaagtcgggt attacaacgt ctatgccaag   1920
aagggagaaa gactcttcat caacgaggag aaaatcctgt ggagtgggtt ctccagggag   1980
gtgcccttct ccaactgcag ccgagactgc ctggcaggga ccaggaaagg gatcattgag   2040
ggggagccca cctgctgctt tgagtgtgtg gagtgtcctg atggggagta tagtgatgag   2100
acagatgcca gtgcctgtaa caagtgccca gatgacttct ggtccaatga gaaccacacc   2160
tcctgcattg ccaaggagat cgagtttctg tcgtggacgg agcccttgg gatcgcactc   2220
accctctttg ccgtgctggg cattttcctg acagcctttg tgctgggtgt gtttatcaag   2280
ttccgcaaca cacccattgt caaggccacc aaccgagagc tctcctacct cctcctcttc   2340
tccctgctct gctgcttctc cagctccctg ttcttcatcg gggagcccca ggactggacg   2400
tgccgcctgc gccagccggc ctttggcatc agcttcgtgc tctgcatctc atgcatcctg   2460
gtgaaaacca accgtgtcct cctggtgttt gaggccaaga tccccaccag cttccaccgc   2520
aagtggtggg gctcaacct gcagttcctg ctggttttcc tctgcacctt catgcagatt   2580
gtcatctgtg tgatctggct ctacaccgcg cccccctcaa gctaccgcaa ccaggagctg   2640
gaggatgaga tcatcttcat cacgtgccac gagggctccc tcatggccct gggcttcctg   2700
atcggctaca cctgcctgct ggctgccatc tgcttcttct tgccttcaa gtcccggaag   2760
ctgccggaga acttcaatga agccaagttc atcaccttca gcatgctcat cttcttcatc   2820
gtctggatct ccttcattcc agcctatgcc agcacctatg gcaagtttgt ctctgccgta   2880
gaggtgattg ccatcctggc agccagcttt ggcttgctgg cgtgcatctt cttcaacaag   2940
atctacatca ttctcttcaa gccatcccgc aacaccatcg aggaggtgcg ttgcagcacc   3000
gcagctcacg ctttcaaggt ggctgcccgg gccacgctgc gccgcagcaa cgtctcccgc   3060
aagcggtcca gcagccttgg aggctccacg ggatccaccc cctcctcctc catcagcagc   3120
aagagcaaca gcgaagaccc attcccacag cccgagaggc agaagcagca gcagccgctg   3180
gccctaaccc agcaagagca gcagcagcag cccctgaccc tcccacagca gcaacgatct   3240
cagcagcagc ccagatgcaa gcagaaggtc atctttggca gcggcacggt caccttctca   3300
ctgagctttg atgagcctca gaagaacgcc atggcccaca gaattctac gcaccagaac   3360
tccctggagg cccagaaaag cagcgatacg ctgaccgac accagccatt actccgctg   3420
cagtgcgggg aaacggactt agatctgacc gtccaggaaa caggtctgca aggacctgtg   3480
ggtggagacc agcggccaga ggtggaggac cctgaagagt tgtccccagc acttgtagtg   3540
tccagttcac agagctttgt catcagtggt ggaggcagca ctgttacaga aaacgtagtg   3600
aattcataaa atggaaggag aagactgggc tagggagaat gcagagaggt ttcttggggt   3660
cccagggatg aggaatcgcc ccagactcct ttcctctgag gaagaaggga taatagacac   3720
atcaaatgcc ccgaatttag tcacaccatc ttaaatgaca gtgaattgac ccatgttccc   3780
```

-continued

```
tttaaaatta aaaaaaagaa gagccttgtg tttctgtggt tgcatttgtc aaagcattga    3840
gatctccacg gtcagatttg ctgttcaccc acatctaatg tctcttcctc tgttctatcc    3900
cacccaacag ctcagagatg aaactatggc tttaaactac cctccagagt gtgcagactg    3960
atgggacatc aaatttgcca ccactagagc tgagagtctg aaagacagaa tgtcaccagt    4020
cctgcccaat gccttgacaa cagactgaat tttaaatgtt cacaacataa ggagaatgta    4080
tctcctccta tttatgaaaa ccatatgata ttttgtctcc tacctgctgc tgctattatg    4140
taacatccag aaggtttgca cccctcctat accatatgtc tgcttctgtc caggacatga    4200
tactgatgcc atgtttagat tccaggatca caagaatcac ctcaaattgt taggaaggga    4260
ctgcataaac caatgagctg tatctgtaat taatattcct atatgtagct ttatccttag    4320
gaaaatgctt ctgttgtaat agtccatgga caatataaac tgaaaaatgt cagtctggtt    4380
tatataaggc agtattattg agctctattt ccccacccca ctatcctcac tcccataagc    4440
taagccttat gtgagcccct tcagggactc aagggtccag aagtccctcc catctctacc    4500
ccaaagaatt cctgaagcca gatccaccct atccctgtac agagtaagtt ctcaattatt    4560
ggcctgctaa tagctgctag ggtaggaaag cgtggttcca agaaagatcc accctcaaat    4620
gtcagagcta tgttccctcc agcagtggta ttaatactgc cggtcaccca ggctctggag    4680
ccagagagac agaccggggt tcaagccatg gcttcgtcat ttgcaagctg agtgactgta    4740
ggcagggaac cttaacctct ctaagccaca gcttcttcat ctttaaaata aggataataa    4800
tcattccttc ccctcagagc tcttatgtgg attaaacgag ataatgtata taaagtactt    4860
tagcctggta cctagcacac aataagcatt caataaatat tagttaatat tat           4913
```

<210> SEQ ID NO 2
<211> LENGTH: 1078
<212> TYPE: PRT
<213> ORGANISM: Homo sapiens

<400> SEQUENCE: 2

```
Met Ala Phe Tyr Ser Cys Cys Trp Val Leu Leu Ala Leu Thr Trp His
  1               5                  10                  15

Thr Ser Ala Tyr Gly Pro Asp Gln Arg Ala Gln Lys Lys Gly Asp Ile
             20                  25                  30

Ile Leu Gly Gly Leu Phe Pro Ile His Phe Gly Val Ala Ala Lys Asp
         35                  40                  45

Gln Asp Leu Lys Ser Arg Pro Glu Ser Val Glu Cys Ile Arg Tyr Asn
     50                  55                  60

Phe Arg Gly Phe Arg Trp Leu Gln Ala Met Ile Phe Ala Ile Glu Glu
 65                  70                  75                  80

Ile Asn Ser Ser Pro Ala Leu Leu Pro Asn Leu Thr Leu Gly Tyr Arg
                 85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175
```

-continued

```
Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
            245                 250                 255

Glu Val Ile Gln Asn Ser Thr Ala Lys Val Ile Val Phe Ser Ser
        260                 265                 270

Gly Pro Asp Leu Glu Pro Leu Ile Lys Glu Ile Val Arg Arg Asn Ile
    275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Thr Ile Gly Phe
305                 310                 315                 320

Ala Leu Lys Ala Gly Gln Ile Pro Gly Phe Arg Glu Phe Leu Lys Lys
            325                 330                 335

Val His Pro Arg Lys Ser Val His Asn Gly Phe Ala Lys Glu Phe Trp
        340                 345                 350

Glu Glu Thr Phe Asn Cys His Leu Gln Glu Gly Ala Lys Gly Pro Leu
            355                 360                 365

Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
            405                 410                 415

Ser Tyr Asn Val Tyr Leu Ala Val Tyr Ser Ile Ala His Ala Leu Gln
        420                 425                 430

Asp Ile Tyr Thr Cys Leu Pro Gly Arg Gly Leu Phe Thr Asn Gly Ser
    435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
            485                 490                 495

Ser Pro Glu Asp Gly Ser Ile Val Phe Lys Glu Val Gly Tyr Tyr Asn
        500                 505                 510

Val Tyr Ala Lys Lys Gly Glu Arg Leu Phe Ile Asn Glu Glu Lys Ile
    515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
            565                 570                 575

Thr Asp Ala Ser Ala Cys Asn Lys Cys Pro Asp Asp Phe Trp Ser Asn
        580                 585                 590

Glu Asn His Thr Ser Cys Ile Ala Lys Glu Ile Glu Phe Leu Ser Trp
```

-continued

```
            595                 600                 605
Thr Glu Pro Phe Gly Ile Ala Leu Thr Leu Phe Ala Val Leu Gly Ile
    610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
            645                 650                 655

Ser Leu Leu Cys Cys Phe Ser Ser Leu Phe Phe Ile Gly Glu Pro
            660                 665                 670

Gln Asp Trp Thr Cys Arg Leu Arg Gln Pro Ala Phe Gly Ile Ser Phe
            675                 680                 685

Val Leu Cys Ile Ser Cys Ile Leu Val Lys Thr Asn Arg Val Leu Leu
            690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
            755                 760                 765

Ser Leu Met Ala Leu Gly Phe Leu Ile Gly Tyr Thr Cys Leu Leu Ala
    770                 775                 780

Ala Ile Cys Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
            835                 840                 845

Leu Ala Cys Ile Phe Phe Asn Lys Ile Tyr Ile Ile Leu Phe Lys Pro
    850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Pro Gln Pro Glu
            915                 920                 925

Arg Gln Lys Gln Gln Pro Leu Ala Leu Thr Gln Gln Glu Gln Gln
    930                 935                 940

Gln Gln Pro Leu Thr Leu Pro Gln Gln Arg Ser Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Gly Asn Ser
            980                 985                 990

Thr His Gln Asn Ser Leu Glu Ala Gln Lys Ser Ser Asp Thr Leu Thr
        995                 1000                1005

Arg His Gln Pro Leu Leu Pro Leu Gln Cys Gly Glu Thr Asp Leu Asp
    1010                1015                1020
```

```
Leu Thr Val Gln Glu Thr Gly Leu Gln Gly Pro Val Gly Gly Asp Gln
1025                1030                1035                1040

Arg Pro Glu Val Glu Asp Pro Glu Glu Leu Ser Pro Ala Leu Val Val
            1045                1050                1055

Ser Ser Ser Gln Ser Phe Val Ile Ser Gly Gly Ser Thr Val Thr
        1060                1065                1070

Glu Asn Val Val Asn Ser
    1075

<210> SEQ ID NO 3
<211> LENGTH: 3783
<212> TYPE: DNA
<213> ORGANISM: Homo sapiens

<400> SEQUENCE: 3
```

| | | | | | |
|---|---|---|---|---|---|
| caacaggcac | ctggctgcag | ccaggaagga | ccgcacgccc | tttcgcgcag | gagagtggaa | 60 |
| ggagggagct | gtttgccagc | accgaggtct | tgcggcacag | gcaacgcttg | acctgagtct | 120 |
| tgcagaatga | aaggcatcac | aggaggcctc | tgcatgatgt | ggcttccaaa | gactcaagga | 180 |
| ccacccacat | tacaagtctg | gattgaggaa | ggcagaaatg | gagattcaaa | caccacgtct | 240 |
| tctattattt | tattaatcaa | tctgtagaca | tgtgtcccca | ctgcagggag | tgaactgctc | 300 |
| caagggagaa | acttctggga | gcctccaaac | tcctagctgt | ctcatccctt | gccctggaga | 360 |
| gacggcagaa | ccatggcatt | ttatagctgc | tgctgggtcc | tcttggcact | cacctggcac | 420 |
| acctctgcct | acgggccaga | ccagcgagcc | caaaagaagg | gggacattat | ccttgggggg | 480 |
| ctctttccta | ttcattttgg | agtagcagct | aaagatcaag | atctcaaatc | aaggccggag | 540 |
| tctgtggaat | gtatcaggta | taatttccgt | gggtttcgct | ggttacaggc | tatgatattt | 600 |
| gccatagagg | agataaacag | cagcccagcc | cttcttccca | acttgacgct | gggatacagg | 660 |
| atatttgaca | cttgcaacac | cgtttctaag | gccttggaag | ccaccctgag | ttttgttgct | 720 |
| caaaacaaaa | ttgattcttt | gaaccttgat | gagttctgca | actgctcaga | gcacattccc | 780 |
| tctacgattg | ctgtggtggg | agcaactggc | tcaggcgtct | ccacggcagt | ggcaaatctg | 840 |
| ctggggctct | tctacattcc | ccaggtcagt | tatgcctcct | ccagcagact | cctcagcaac | 900 |
| aagaatcaat | tcaagtcttt | cctccgaacc | atccccaatg | atgagcacca | ggccactgcc | 960 |
| atggcagaca | tcatcgagta | tttccgctgg | aactgggtgg | gcacaattgc | agctgatgac | 1020 |
| gactatgggc | ggccggggat | tgagaaattc | cgagaggaag | ctgaggaaag | ggatatctgc | 1080 |
| atcgacttca | gtgaactcat | ctcccagtac | tctgatgagg | aagagatcca | gcatgtggta | 1140 |
| gaggtgattc | aaaattccac | ggccaaagtc | atcgtggttt | tctccagtgg | cccagatctt | 1200 |
| gagcccctca | tcaaggagat | tgtccggcgc | aatatcacgg | gcaagatctg | gctggccagc | 1260 |
| gaggcctggg | ccagctcctc | cctgatcgcc | atgcctcagt | acttccacgt | ggttggcggc | 1320 |
| accattggat | tcgctctgaa | ggctgggcag | atcccaggct | tccgggaatt | cctgaagaag | 1380 |
| gtccatccca | ggaagtctgt | ccacaatggt | tttgccaagg | agttttggga | agaaacattt | 1440 |
| aactgccacc | tccaagaagg | tgcaaaagga | cctttacctg | tggacacctt | tctgagaggt | 1500 |
| cacgaagaaa | gtggcgacag | gtttagcaac | agctcgacag | ccttccgacc | cctctgtaca | 1560 |
| ggggatgaga | acatcagcag | tgtcgagacc | ccttacatag | attacacgca | tttacggata | 1620 |
| tcctacaatg | tgtacttagc | agtctactcc | attgccacg | ccttgcaaga | tatatatacc | 1680 |
| tgcttacctg | ggagagggct | cttcaccaat | ggctcctgtg | cagacatcaa | gaaagttgag | 1740 |

-continued

```
gcgtggcagg tcctgaagca cctacggcat ctaaacttta caaacaatat gggggagcag    1800 gtgaccttttg atgagtgtgg tgacctggtg gggaactatt ccatcatcaa ctggcacctc    1860
tccccagagg atggctccat cgtgtttaag aagtcgggt attacaacgt ctatgccaag      1920
aagggagaaa gactcttcat caacgaggag aaaatcctgt ggagtgggtt ctccagggag    1980
gtgcccttct ccaactgcag ccgagactgc ctggcaggga ccaggaaagg gatcattgag    2040
ggggagccca cctgctgctt tgagtgtgtg gagtgtcctg atggggagta tagtgatgag    2100
acagatgcca gtgcctgtaa caagtgccca gatgacttct ggtccaatga aaccacacc    2160 tcctgcattg ccaaggagat cgagtttctg tcgtggacgg agccctttgg gatcgcactc    2220
accctctttg ccgtgctggg cattttcctg acagcctttg tgctgggtgt gtttatcaag    2280
ttccgcaaca cacccattgt caaggccacc aaccgagagc tctcctacct cctcctcttc    2340
tccctgctct gctgcttctc cagctccctg ttcttcatcg gggagcccca ggactggacg    2400
tgccgcctgc gccagccggc ctttggcatc agcttcgtgc tctgcatctc atgcatcctg    2460
gtgaaaacca accgtgtcct cctggtgttt gaggccaaga tccccaccag cttccaccgc    2520
aagtggtggg gctcaacct gcagttcctg ctggtttttcc tctgcacctt catgcagatt    2580
gtcatctgtg tgatctggct ctacaccgcg ccccctcaa gctaccgcaa ccaggagctg    2640
gaggatgaga tcatcttcat cacgtgccac gagggctccc tcatggccct gggcttcctg    2700
atcggctaca cctgcctgct ggctgccatc tgcttcttct ttgccttcaa gtcccggaag    2760
ctgccggaga acttcaatga agccaagttc atcaccttca gcatgctcat cttcttcatc    2820
gtctggatct ccttcattcc agcctatgcc agcacctatg gcagtttgt ctctgccgta    2880 gaggtgattg ccatcctggc agccagcttt ggcttgctgg cgtgcatctt cttcaacaag    2940
atctacatca ttctcttcaa gccatcccgc aacaccatcg aggaggtgcg ttgcagcacc    3000
gcagctcacg ctttcaaggt ggctgccgg gccacgctgc gccgcagcaa cgtctcccgc    3060
aagcggtcca gcagccttgg aggctccacg ggatccaccc cctcctcctc catcagcagc    3120
aagagcaaca cgaagaccc attcccacag cccgagaggc agaagcagca gcagccgctg    3180
gccctaaccc agcaagagca gcagcagcag cccctgaccc tcccacagca gcaacgatct    3240
cagcagcagc ccagatgcaa gcagaaggtc atctttggca gcggcacggt caccttctca    3300
ctgagctttg atgagcctca gaagaacgcc atggcccacg ggaattctac gcaccagaac    3360
tccctggagg cccagaaaag cagcgatacg ctgacccgac accagccatt actcccgctg    3420
cagtgcgggg aaacggactt agatctgacc gtccaggaaa caggtctgca aggacctgtg    3480
ggtggagacc agcggccaga ggtggaggac cctgaagagt tgtccccagc acttgtagtg    3540
tccagttcac agagctttgt catcagtggt ggaggcagca ctgttacaga aaacgtagtg    3600
aattcataaa atggaaggag aagactgggc tagggagaat gcagagaggt ttcttggggt    3660
cccagggatg aggaatcgcc ccagactcct ttcctctgag aagaaggga taatagacac    3720 atcaaatgcc ccgaatttag tcacaccatc ttaaatgaca gtgaattgac ccatgttccc    3780
ttt                                                                  3783
```

<210> SEQ ID NO 4
<211> LENGTH: 1078
<212> TYPE: PRT
<213> ORGANISM: Homo sapiens

<400> SEQUENCE: 4

Met Ala Phe Tyr Ser Cys Cys Trp Val Leu Leu Ala Leu Thr Trp His

-continued

|   1 |     |     |     |   5 |     |     |     |     |  10 |     |     |     |     |  15 |     |
|-----|-----|-----|-----|-----|-----|-----|-----|-----|-----|-----|-----|-----|-----|-----|-----|
| Thr | Ser | Ala | Tyr | Gly | Pro | Asp | Gln | Arg | Ala | Gln | Lys | Lys | Gly | Asp | Ile |
|     |     |     |  20 |     |     |     |     |  25 |     |     |     |     |  30 |     |     |

Ile Leu Gly Gly Leu Phe Pro Ile His Phe Gly Val Ala Ala Lys Asp
         35                  40                  45

Gln Asp Leu Lys Ser Arg Pro Glu Ser Val Glu Cys Ile Arg Tyr Asn
     50              55                  60

Phe Arg Gly Phe Arg Trp Leu Gln Ala Met Ile Phe Ala Ile Glu Glu
 65              70                  75                      80

Ile Asn Ser Ser Pro Ala Leu Leu Pro Asn Leu Thr Leu Gly Tyr Arg
                 85                  90                      95

Ile Phe Asp Thr Cys Asn Thr Val Ser Lys Ala Leu Glu Ala Thr Leu
             100                 105                 110

Ser Phe Val Ala Gln Asn Lys Ile Asp Ser Leu Asn Leu Asp Glu Phe
         115                 120                 125

Cys Asn Cys Ser Glu His Ile Pro Ser Thr Ile Ala Val Val Gly Ala
     130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
             165                 170                 175

Lys Asn Gln Phe Lys Ser Phe Leu Arg Thr Ile Pro Asn Asp Glu His
             180                 185                 190

Gln Ala Thr Ala Met Ala Asp Ile Ile Glu Tyr Phe Arg Trp Asn Trp
         195                 200                 205

Val Gly Thr Ile Ala Ala Asp Asp Tyr Gly Arg Pro Gly Ile Glu
         210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
             245                 250                 255

Glu Val Ile Gln Asn Ser Thr Ala Lys Val Ile Val Phe Ser Ser
         260                 265                 270

Gly Pro Asp Leu Glu Pro Leu Ile Lys Glu Ile Val Arg Arg Asn Ile
275                 280                 285

Thr Gly Lys Ile Trp Leu Ala Ser Glu Ala Trp Ala Ser Ser Ser Leu
         290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
             325                 330                 335

Val His Pro Arg Lys Ser Val His Asn Gly Phe Ala Lys Glu Phe Trp
         340                 345                 350

Glu Glu Thr Phe Asn Cys His Leu Gln Glu Gly Ala Lys Gly Pro Leu
             355                 360                 365

Pro Val Asp Thr Phe Leu Arg Gly His Glu Glu Ser Gly Asp Arg Phe
     370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                 405                 410                 415

Ser Tyr Asn Val Tyr Leu Ala Val Tyr Ser Ile Ala His Ala Leu Gln
             420                 425                 430

-continued

```
Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Val Pro Phe Ser Asn Cys Ser Arg
530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
        595                 600                 605

Thr Glu Pro Phe Gly Ile Ala Leu Thr Leu Phe Ala Val Leu Gly Ile
610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
            660                 665                 670

Gln Asp Trp Thr Cys Arg Leu Arg Gln Pro Ala Phe Gly Ile Ser Phe
        675                 680                 685

Val Leu Cys Ile Ser Cys Ile Leu Val Lys Thr Asn Arg Val Leu Leu
690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
        755                 760                 765

Ser Leu Met Ala Leu Gly Phe Leu Ile Gly Tyr Thr Cys Leu Leu Ala
770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
        835                 840                 845
```

-continued

```
Leu Ala Cys Ile Phe Phe Asn Lys Ile Tyr Ile Ile Leu Phe Lys Pro
    850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Pro Gln Pro Glu
        915                 920                 925

Arg Gln Lys Gln Gln Pro Leu Ala Leu Thr Gln Gln Glu Gln Gln
    930                 935                 940

Gln Gln Pro Leu Thr Leu Pro Gln Gln Arg Ser Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Arg Asn Ser
            980                 985                 990

Thr His Gln Asn Ser Leu Glu Ala Gln Lys Ser Ser Asp Thr Leu Thr
        995                1000                1005

Arg His Gln Pro Leu Leu Pro Leu Gln Cys Gly Glu Thr Asp Leu Asp
    1010                1015                1020

Leu Thr Val Gln Glu Thr Gly Leu Gln Gly Pro Val Gly Gly Asp Gln
1025                1030                1035                1040

Arg Pro Glu Val Glu Asp Pro Gly Glu Leu Ser Pro Ala Leu Val Val
                1045                1050                1055

Ser Ser Ser Gln Ser Phe Val Ile Ser Gly Gly Gly Ser Thr Val Thr
            1060                1065                1070

Glu Asn Val Val Asn Ser
        1075

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagaaggtca tctttggcag cggca                                           25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcttcctcag aggaaaggag tctgg                                           25
```

EFFICACY OF CALCIMIMETIC AGENTS

CROSS-REFERENCE TO RELATED APPLICATION

This application claims the benefit of U.S. Provisional Application No. 60/735,608, filed Nov. 10, 2005, which is hereby incorporated herein by this reference.

BACKGROUND

Secondary hyperparathyroidism (sHPT), i.e. the over-production of parathyroid hormone (PTH) by the parathyroid glands, affects the majority of untreated end-stage renal failure patients. If this condition is untreated, it leads to bone pain, fractures, cognitive impairment and depression, thus reducing the quality of life of and increasing mortality of such patients. It is also associated with hypercalcaemia and higher arterial calcification scores, and it is an independent cardiovascular risk factor in itself. As early as stage II in the course of renal insufficiency, PTH levels start to rise with the declining ability of the kidneys to excrete phosphorus. In addition to this, with the declining ability of the kidneys to hydroxylate 25-OH Vitamin D3, levels of the potent PTH suppressor 1,25-OH Vitamin D3 fall below normal unless it is supplemented. In primary hyperparathyroidism (pHPT), PTH overproduction occurs in adenomatous chief cells of the parathyroid glands without being triggered by renal insufficiency. If in the course of secondary HPT the glands lose their responsiveness to regulatory mechanisms, this is referred to as tertiary HPT.

SUMMARY

The present disclosure describes systems and methods for testing or predicting the efficacy of certain drugs in treating hyperparathyroidism, especially secondary hyperparathyroidism (sHPT). The inventor has found that a polymorphism in the calcium-sensing receptor gene (CaSR) is predictive of the efficacy of the calcimimetic drug cinacalcet in treating sHPT. This method may be used to test related molecules and salts as candidate therapeutics for forms of hyperparathyroidism, and may be used to assess an agent's efficacy in treating other forms of hyperparathyroidism, as well as other conditions that involve derangements of calcium homeostasis. Compositions and kits for the practice of the methods are also described herein.

BRIEF DESCRIPTION OF THE DRAWINGS

FIGS. 7A-B show the cDNA (SEQ ID NO: 1) and amino-acid (SEQ ID NO: 2) sequences, respectively, for human CaSR-$^{990}$Gly.

FIGS. 8A-B show the cDNA (SEQ ID NO: 3) and amino-acid (SEQ ID NO: 4) sequences, respectively, for human CaSR-$^{990}$Arg.

DETAILED DESCRIPTION

Figure 1:
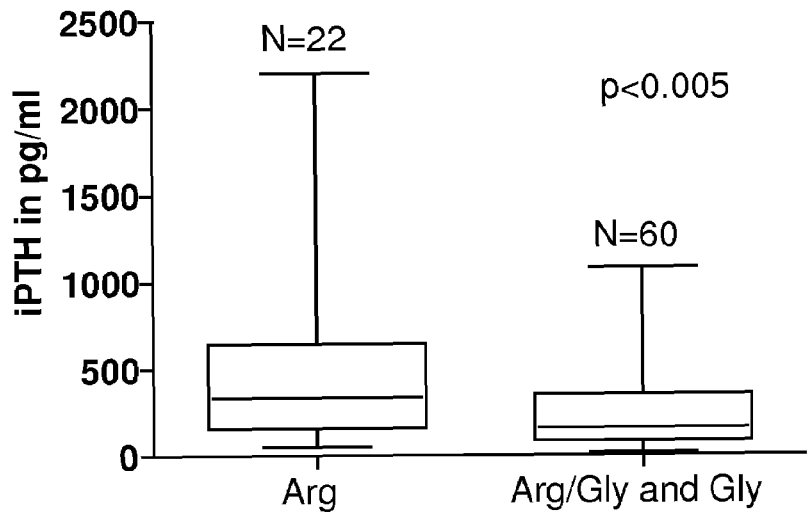
FIG. 1 depicts a comparison of iPTH levels in subjects homozygous for CaSR-$^{990}$Arg to subjects hetero- or homozygous for CaSR-$^{990}$Gly.

For convenience, certain terms employed in the specification, examples and appended claims are defined here.

The singular forms "a", "an", and "the" include plural references unless the context clearly dictates otherwise.

"Allele", which is used interchangeably herein with "allelic variant", refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene may differ from each other in a single nucleotide, or several nucleotides, and may include substitutions, deletions, and insertions of nucleotides. An allele of a gene may also be a form of a gene containing a mutation.

"Calcimimetic drug" is defined as any compound and pharmaceutically acceptable salts thereof disclosed in any of the following documents: U.S. patent application Ser. No. 07/749,451, filed on Aug. 23, 1991; 07/834,044, filed on Feb. 11, 1992; 07/934,161 filed on Aug. 21, 1992; 08/009,389 filed on Feb. 23, 1993; 08/017,127 filed on Feb. 12, 1993; 08/141,248 filed on Oct. 22, 1993; 08/292,827 filed on Aug. 19, 1994; 08/321,577 filed on Oct. 11, 1994; U.S. Pat. Nos. 5,688,938; 5,763,569; 5,858,684; 6,001,884; 6,011,068; 6,031,003; 6,313,146. Each of the aforementioned U.S. patent applications and patents is hereby incorporated herein by reference.

"Cinacalcet" refers to cinacalcet HCl (Sensipar®, Mimpara®, AMG 073, KRN 1493, NPS 1493, Parareg®).

"Gene" or "recombinant gene" refers to a nucleic acid molecule comprising an open reading frame and including at least one exon and (optionally) an intron sequence. "Intron" refers to a DNA sequence present in a given gene which is spliced out during mRNA maturation.

The term "hyperparathyroidism" refers to production of excess parathyroid hormone. In some cases, parathyroid hormone is produced without regard to the calcium levels. This is called "primary hyperparathyroidism" and is caused by enlargement of one or more of the parathyroid glands. "Secondary hyperparathyroidism" occurs when the body produces extra parathyroid hormone because the calcium levels are too low. If the parathyroid glands continue to produce too much parathyroid hormone even though the calcium level is back to normal, this is called "tertiary hyperthyroidism" and occurs especially in patients with kidney problems. The term "hyperparathyroidism" when used herein without the term "primary", "secondary", or "tertiary" is meant to be inclusive of all of the forms of hyperparathyroidism.

A "patient", "subject" or "host" to be treated by the subject method may mean either a human or non-human animal.

The phrase "pharmaceutically acceptable salt," as used herein, refers to a pharmaceutically acceptable organic or inorganic acid or base salt of an organic chemical compound. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. The counterion may be any organic or inorganic moiety that stabilizes the charge on the parent compound. Furthermore, a pharmaceutically acceptable salt may have more than one charged atom in its structure. In this instance the pharmaceutically acceptable salt can have multiple counterions. Hence, a pharmaceutically acceptable salt can have one or more charged atoms and/or one or more counterions.

A single-nucleotide polymorphism (SNP) has been described in exon 7 of the CaSR gene, whereby the amino acid at position 990 may be glycine or arginine. FIG. 7A shows a cDNA sequence for the $^{990}$Gly form (Genbank accession number NM_000388.1, SEQ ID NO:3), in which a guanine base at position 3340 (shown in FIG. 7A in inverse) corresponds to the first position of codon 990 (outlined in FIG. 7A); the codon "ggg" codes for glycine. FIG. 7B shows the amino acid sequence for the $^{990}$Gly form (Genbank accession number NP_000379.1, SEQ ID NO: 2). FIG. 8A shows a cDNA sequence for the $^{990}$Arg form (Genbank accession number NM_000388.2, SEQ ID NO: 1), in which an adenine base at position 3340 (shown in FIG. 8A in inverse) corresponds to the first position of codon 990 (outlined in FIG. 8A); the codon "agg" codes for arginine. FIG. 8B shows the amino acid sequence for the $^{990}$Arg form (Genbank accession number NP_000379.2, also deposited as UniProt P41180, SEQ ID NO: 4). Consequently, a subject, such as a human subject, may have one of three different genotypes: Arg-Arg, Arg-Gly, or Gly-Gly. This is discussed in greater detail in Rothe et al., "Calcium-sensing receptor gene polymorphism Arg$^{990}$Gly and its possible effect on response to cinacalcet HCl," *Pharmacogenet. Genomics* (2005) 15(1):29-34, which is hereby incorporated herein by this reference. CaSR-$^{990}$Gly is the more prevalent type in Asian populations, while CaSR-$^{990}$Arg is more prevalent in non-Asian populations. Incorporated by reference in their entirety are any polynucleotide and polypeptide sequences which reference an accession number correlating to an entry in the public database of the National Center for Biotechnology Information (NCBI) on the world wide web at ncbi.nlm.nih.gov.

Until recently, treatment options for sHPT consisted of phosphate binders and vitamin D supplementation plus parathyroidectomy as an ultima ratio. However, according to a survey of 288 facilities/749 dialysis patients, only 29% had average PTH levels within the defined target range (Johnson, C. A. (2002) Analysis of renal bone disease treatment in dialysis patients. *Am J Kidney Dis.* 39, 1270-1277).

Now nephrologists have a new and potent treatment option with cinacalcet HCl (Sensipar®, Mimpara®, AMG 073, KRN 1493, NPS 1493, Parareg®), the first calcimimetic agent available for the therapy of secondary hyperparathyroidism (sHPT) and palliative treatment of parathyroid carcinoma. It was approved by the US Food and Drug Administration in March 2004. Its target is the extracellular calcium-sensing receptor (CaSR). Cinacalcet binds to the extracellular portion of the receptor and allosterically increases its sensitivity towards calcium ions (its "calcium sensitivity"), i.e. it shifts the calcium set-point to the left. The set-point is defined as the serum ionized calcium concentration, which leads to a serum PTH level half way between maximum and minimum levels. If this point shifts to the left on the calcium concentration axis (x-axis), PTH secretion will be suppressed at normal or even low calcium levels, as if hypercalcaemia was present.

Analysis of data pooled from three phase III studies of cinacalcet (described in more detailed below) shows that patients treated with cinacalcet had a 50% reduction in PTH relative to baseline values compared with an increase of 4.1% in the standard treatment control group. Forty percent of Cinacalcet-treated patients and 5% of control patients achieved the predefined PTH target. Thirty-three percent of Cinacalcet-treated patients and 9% of control patients had a mean PTH value of 150 to 300 pg/mL (15.9 to 31.8 pmol/L), the K/DOQI-recommended range.

Patients may be genotyped for CaSR allelic status in a number of ways. As used herein, "genotyping a subject (or DNA sample)" means detecting which forms of the allele are present in a subject (or a biological sample).

Polymorphic alleles are typically detected by directly determining the presence of the polymorphic sequence in a polynucleotide or protein from the subject, using any suitable technique as is known in the art. Such a polynucleotide is typically genomic DNA, or a polynucleotide derived from this polynucleotide, such as in a library made using genomic material from the individual (e.g. a cDNA library). Typically the presence of the polymorphism is determined in a method that comprises contacting a polynucleotide or protein of the individual with a specific binding agent for the polymorphism and determining whether the agent binds to the polynucleotide or protein, where the binding indicates that the polymorphism is present. The binding agent may also bind to flanking nucleotides and amino acids on one or both sides of the polymorphism, for example at least 2, 5, 10, 15 or more flanking nucleotide or amino acids in total or on each side. In one embodiment the agent is able to bind the corresponding wild-type sequence by binding the nucleotides or amino acids which flank the polymorphism position, although the manner of binding will be different than the binding of a polymorphic polynucleotide or protein, and this difference will be detectable (for example this may occur in sequence specific PCR as discussed below).

In the case where the presence of the polymorphism is being determined in a polynucleotide it may be detected in the double stranded form, but is typically detected in the single stranded form.

Because the difference in CaSR gene alleles is a single-nucleotide polymorphism, PCR sequencing is a suitable method to genotype the subject. The PCR process is described in e.g., U.S. Pat. Nos. 4,683,195; 4,683,202; and 4,965,188; PCR Technology: Principles and Applications for DNA Amplification (ed. Erlich, Freeman Press, New York, N.Y., 1992); PCR Protocols: A Guide to Methods and Applications (eds. Innis et al., Academic Press, San Diego, Calif. (1990); Mattila et al. Nucleic Acids Res. 19:4967 (1991); Eckert & Kunkel PCR Methods and Applications 1:17 (1991); PCR (eds. McPherson et al., IRL Press, Oxford), each of which is incorporated by this reference in its entirety.

An exemplary PCR genotyping procedure, in brief, is as follows:

DNA or cDNA is obtained from the subject to be studied. DNA may be obtained from a tissue sample. A common sample is lymphocytes isolated from blood (starting with whole blood collected in EDTA tubes, cells are separated by 10 min centrifugation at 1100×g. The fraction containing lymphocytes and platelets is separated from red cells and granulocytes by gradient centrifugation for instance with Ficoll Paque™ plus). DNA extraction from the cell suspension is performed by a variety of techniques, for instance using a Genomic DNA Purification kit (Wizard®, Promega, Madison, Wis.). The process includes cell lysis, incubation with RNAse, protein precipitation and finally DNA precipitation with isopropanol and 70% ethanol. The resulting DNA preparation is dissolved in 10 mM Tris buffer plus 1 mM EDTA and can be stored at −20° C. cDNA may be obtained by isolating RNA from a sample (such as by using TriZOL® reagent and the process described in U.S. Pat. No. 5,346,994, which is hereby incorporated herein by reference) and synthesizing the first strand using well-known reverse transcriptase techniques.

The DNA or cDNA in the region surrounding that which encodes amino acid residue 990 is amplified using the polymerase chain reaction (PCR). In one embodiment, PCR may be performed with Taq DNA polymerase (for instance Roche Diagnostics GmbH, Mannheim, Germany) in an amplifier (for instance Perkin Elmer GeneAmp PCR System 2400, Norwalk, Cincinnati), using the following primers: 5'-CAGAAGGTCATCTTTGGCAGCGGCA-3' (forward) (SEQ ID NO: 5) (the position of the forward primer in the CaSR cDNA is indicated by single underlining in FIGS. 7A and 8A) and 5'-TCTTCCTCAGAGGAAAGGAGTCTGG-3' (reverse) (SEQ ID NO: 6) (the position of the reverse primer's reverse complement in the CaSR gene is indicated by double underlining in FIGS. 7A and 8A). Primers may differ between some nucleotides, as long as position 990 is still located between them. The best amplification method is as follows: 92° C. for 3 min, then 25 cycles of 95° C.-68° C.-72° C. (30 sec. each), and 72° C. for 10 min.

The amplified DNA is then sequenced using well-known techniques. Sequencing should be performed with both a sense and an antisense primer, so that single-nucleotide polymorphism findings at the 990 codon can be cross-checked.

Other suitable amplification methods include the ligase chain reaction (LCR) (see Wu and Wallace, Genomics, 1989, vol. 4, pages 560; Landegren et al., Science, 1988, vol. 241, pages 1077; transcription amplification (Kwoh et al., Proc. Natl. Acad. Sci. USA, 1989, vol. 86, page 1173), and self-sustained sequence replication (Guatelli et al., Proc. Nat. Acad. Sci. USA, 1990, vol. 87, page 1874) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Alternatively to PCR amplification and sequencing, position 990 can be visualized by any other method of single-nucleotide polymorphism genotyping known in the art. For example, in situ hybridization with a sequence-specific oligonucleotide probe, bound to a marker which is, for instance, fluorescent, may be used to visualize position 990. Other methods that are well-known in the art include, but are not limited to, matrix-assisted laser desorption/ionization time-of-flight mass spectrometry (MALDI-TOF), dynamic allele-specific hybridization (DASH), pyrosequencing. minisequencing, the invader assay, rolling circle amplification, melting curve analysis (McSNP), multiplex automated primer extension analysis (MAPA), MIP genotyping with molecular inversion probes, the Survivor assay (an SNP detection method based on electrospray ionization mass spectrometry (ESI-MS)), the Qbead system with fluorescent Qdot semiconductor nanocrystals, template-directed dye-terminator incorporation with fluorescence quenching detection (FQ-TDI), SNP genotyping using single-tube fluorescent bidirectional polymerase chain reaction (PCR), multiplexed single-base extension (SBE) genotyping via end-labeled free-solution electrophoresis (ELFSE), molecular beacons and real-time PCR, site-selective RNA scission, the 'ZipCodes'-oligonucleotide ligation assay (OLA) and flow cytometric analysis of fluorescent microspheres, fluorescence polarization, and amplifluor (allele-specific amplification and universal energy-transfer-labeled primers). Such methods are reviewed in *Expert Reviews in Molecular Medicine* (2004 Apr. 1), 6: 1-15, which is expressly incorporated by reference herein in its entirety. Further, antibodies able to distinguish between the different CaSR genes and gene products may be used in methods of determining which CaSR genes or gene products are present in a subject.

Genotyping of the patients studied demonstrates that one reason for variability in the response to cinacalcet is the polymorphism $Arg^{990}Gly$ in the intracellular tail of the CaSR molecule. It is one of three SNP's in exon 7 of the CaSR gene, the other two being $Ala^{986}Ser$ and $Glu^{1011}Gln$. In a study of 7 haemodialysis patients with sHPT who were treated with cinacalcet HCl over a period of two months, bio-intact PTH (biPTH) levels were measured on a weekly basis and cinacalcet doses adjusted according to the treatment goal of biPTH levels <160 pg/ml. One patient was found to be homozygous for the $Arg^{990}Gly$ polymorphism and another was heterozygous for both arginine and glycine alleles. The homozygous patient showed a significantly higher sensitivity to cinacalcet compared to the other patients with consistently stronger biPTH suppression from baseline although he received lower doses of the drug as verified by pill counting.

The test for $Arg^{990}Gly$ polymorphism status can be used to assess the genetic risk for individual patients: carrying two glycine alleles, which are most prevalent in the Asian population, means the lowest risk, carrying two arginine alleles, the highest, and being heterozygote, an intermediate risk. This is demonstrated by data shown in FIG. 1. Random iPTH and alkaline phosphatase levels were taken from 82 patients from 3 New York dialysis units. Both parameters are well established indicators of sHPT. As shown in FIG. 1, random iPTH levels were significantly lower in patients with one or two glycine alleles than in patients with two arginine alleles.

Figure 2:
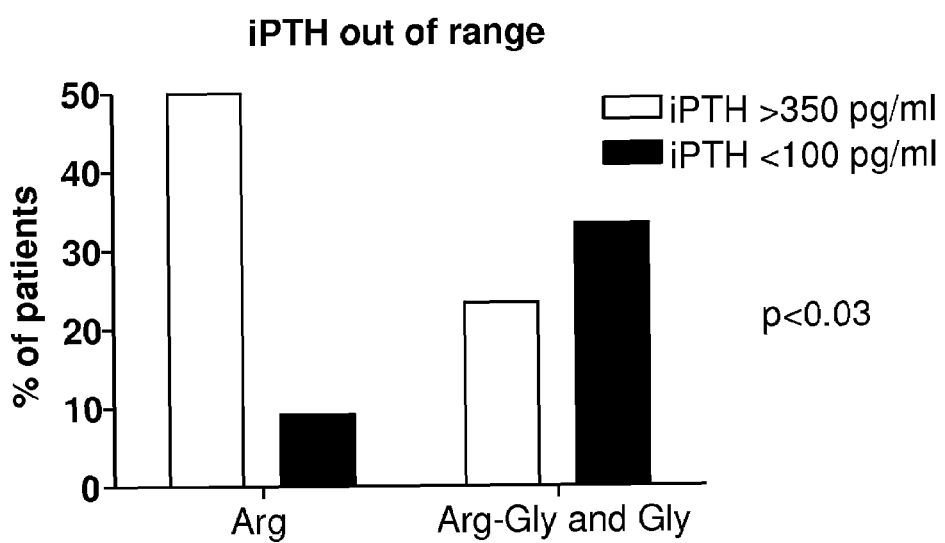
FIG. 2 depicts a comparison of percentages of subjects having iPTH above a target range for subjects homozygous for CaSR-$^{990}$Arg to subjects hetero- or homozygous for CaSR-$^{990}$Gly.

As shown in FIG. 2, higher proportions of patients with two arginine alleles had iPTH levels above the target range of 300 pg/ml as recommended by the K/DOQI guidelines of the ASN, and higher proportions of patients with one or two glycine alleles had levels below the recommended minimum of 150 pg/ml.

Figure 3:
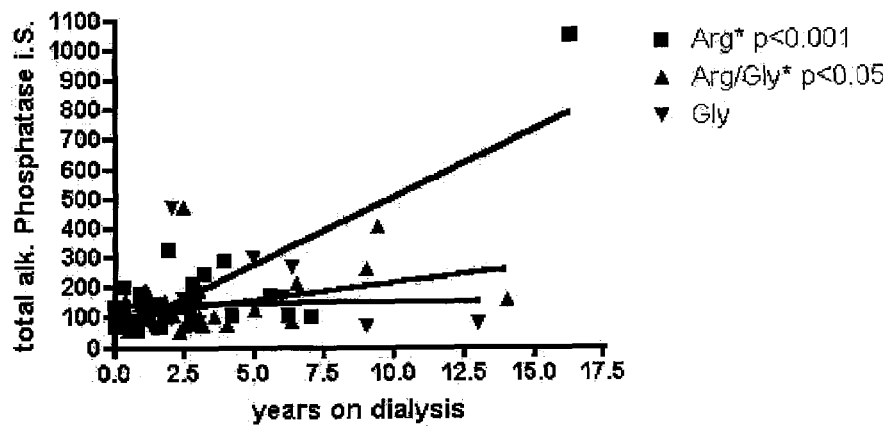
FIG. 3 shows correlations between severity of hyperparathyroidism and number of years on dialysis for different CaSR genotype populations.

As shown in FIG. 3, alkaline phosphatase levels correlate with the number of years, how long the patient has had end-stage kidney disease: the slope is steepest in patients with two arginine alleles, intermediate in heterozygotes and lowest in patients with two glycine alleles.

Figure 4:
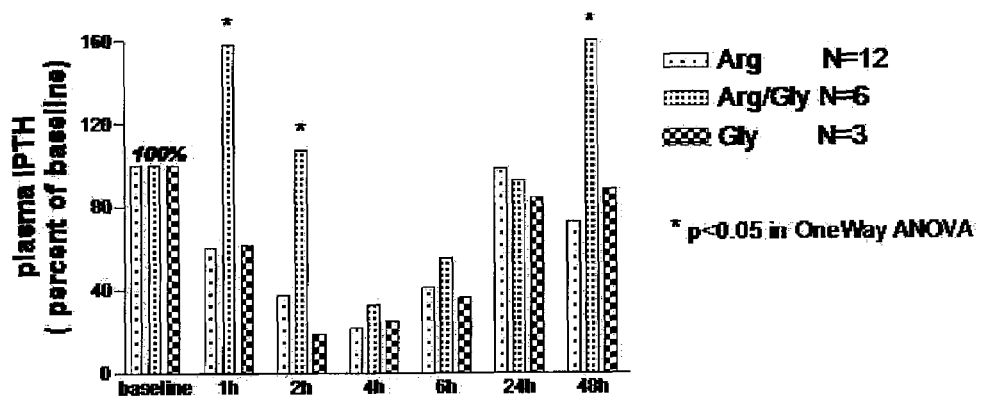
FIG. 4 shows time-course responses to cinacalcet administration for different CaSR genotype populations.
Figure 5:
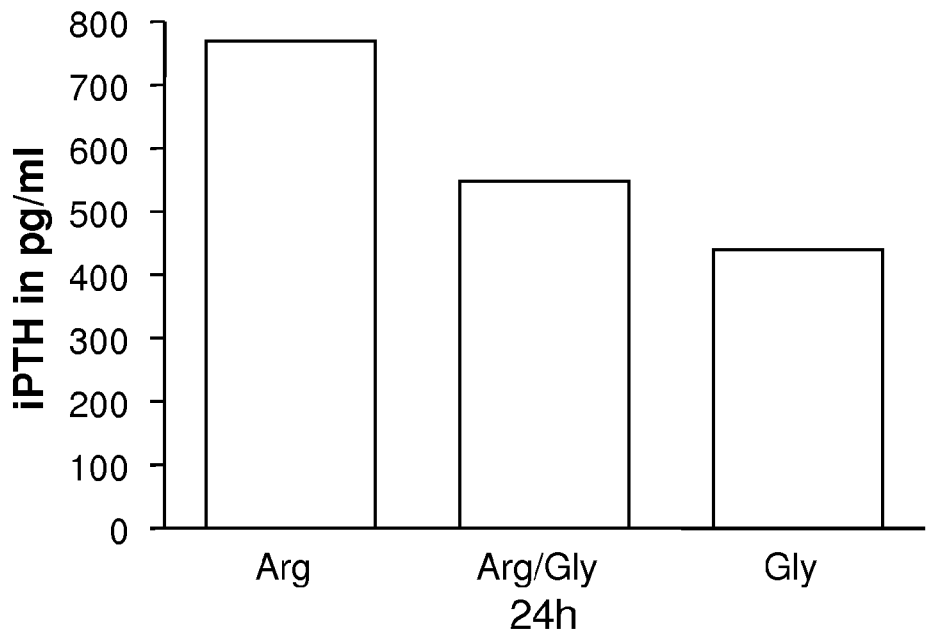
FIG. 5 shows differences in iPTH levels at 24-hours after cinacalcet administration for different CaSR genotype populations.
Figure 6:
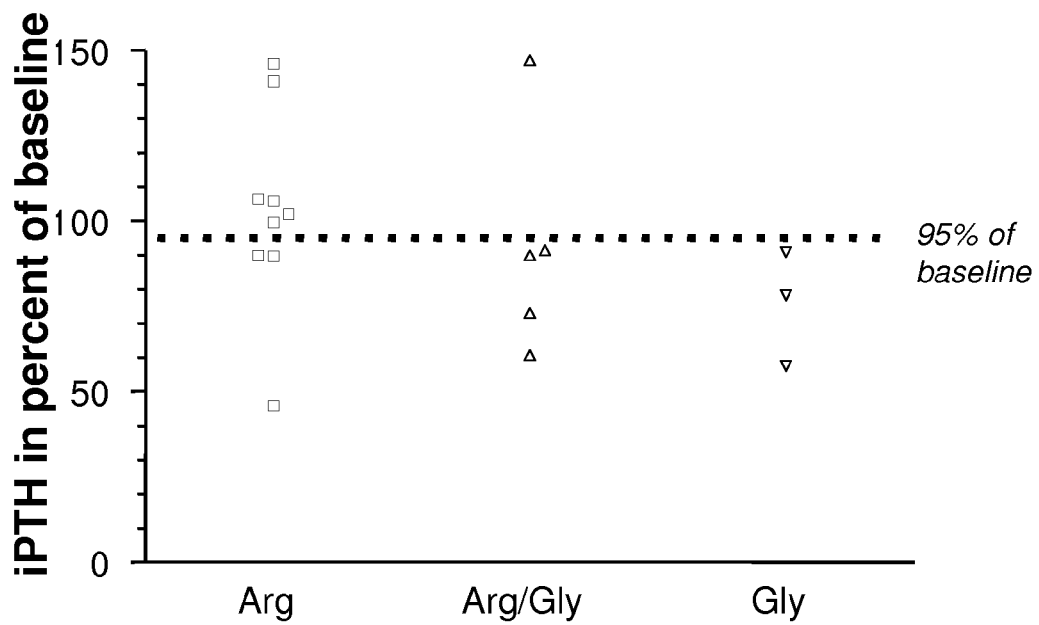
FIG. 6 shows a comparison of efficacy of cinacalcet for different CaSR genotype populations.

A single-dose dose response study of 17 haemodialysis patients with sHPT (latest routine iPTH level ≧300 pg/ml) was performed. Intact PTH suppression after the administration of 60 mg cinacalcet HCl was measured. FIGS. 4-6 show results of this study. While in a subgroup of 9 patients homozygous for the arginine allele only 3 (33%) showed an iPTH suppression by at least 5% of baseline after 24 hours, 7 out of 8 patients (88%) with one or two glycine alleles achieved this target (p<0.05, Fisher's exact test) (FIG. 6). Since cinacalcet is administered as one tablet every 24 hours, this difference does influence the overall response to the drug.

Statistically significant differences between the two groups were also noted in the short term and long term response: a paradoxical initial increase of iPTH above baseline level in the first two hours post dose occurred more often in the Arg$^{990}$Gly heterozygotes (p<0.05 in ANOVA) and at 48 hours post dose iPTH levels were again highest in that group (p<0.05 in ANOVA) (FIG. 4). There were no statistically significant differences between the groups with regard to their baseline iPTH, calcium, concomitant vitamin D analogue doses, phosphate binder doses or the actual plasma cinacalcet levels measured 4 hours after administration of the 60 mg dose.

These results demonstrate that the efficacy of cinacalcet for a given subject can be predicted by the subject's genotype for CaSR: most efficacious for homozygous $^{990}$Gly, intermediate efficacy for heterozygous $^{990}$Gly/$^{990}$Arg, and lowest efficacy for homozygous $^{990}$Arg.

Accordingly, a method of assessing the efficacy of a calcimimetic drug to treat hyperparathyroidism in a subject may include determining which alleles for a calcium-sensitive receptor (CaSR) gene the subject carries; and concluding that the calcimimetic drug will have a first or highest efficacy if the subject has a $^{990}$Gly-$^{990}$Gly genotype, a second or intermediate efficacy if the subject has a $^{990}$Gly-$^{990}$Arg genotype, or a third or lowest efficacy if the subject has a $^{990}$Arg-$^{990}$Arg genotype. In one embodiment, the calcimimetic drug may be cinacalcet or any pharmaceutically acceptable salt thereof.

This method may be applied not only to predicating cinacalcet efficacy, but also to other members of the calcimimetic drug family.

Members of the calcimimetic drug family that may be effective in treating hyperparathyroidism may be assessed by measuring a calcium sensitivity of a calcium-sensitive receptor (CaSR) protein which includes $^{990}$Gly (CaSR-$^{990}$Gly) in the presence of the candidate calcimimetic drug, measuring a calcium sensitivity of a CaSR protein which includes $^{990}$Arg (CaSR-$^{990}$Arg) in the presence of the candidate calcimimetic drug, and concluding that the candidate calcimimetic drug will have a first or highest efficacy if the calcium sensitivity of CaSR-$^{990}$Gly in the presence of the candidate calcimimetic drug exceeds the calcium sensitivity of CaSR-$^{990}$Arg in the presence of the candidate calcimimetic drug, a second or intermediate efficacy if the calcium sensitivity of CaSR-$^{990}$Gly in the presence of the candidate calcimimetic drug is equal or about equal to the calcium sensitivity of CaSR-$^{990}$Arg in the presence of the candidate calcimimetic drug, or a third or lowest efficacy if the calcium sensitivity of CaSR-$^{990}$Gly in the presence of the candidate calcimimetic drug is less than the calcium sensitivity of CaSR-$^{990}$Arg in the presence of the candidate calcimimetic drug.

A variety of assays known to those of skill in the art may be used to determine the calcium sensitivity of the CaSR. Such assays can be carried out either in a cell-free assay system or in an intact cell. Any cell that expresses a CaSR can be used in a cell-based assay system. The CaSR can be naturally occurring in the cell or can be introduced using recombinant techniques as are well-known to those of skill in the art. Either a primary culture or an established cell line, such as CHO or human embryonic kidney 293 cells, can be used.

For example, assays which may be used to assess calcium sensitivity of the CaSR may comprise the use of kinetic, cell-based intracellular calcium-signaling assays (such as monitoring of intracellular calcium, calcium release assays, etc), membrane potential assays, repolarization assays (i.e., measurements of concentration-response and rate-dependence of test compounds on action potential parameters such as resting membrane potential (RMP, mV), action potential amplitude (APA, mV), maximum rate of rise (Vmax, V/s), and action potential duration at 60 and 90% repolarization (APD60 and APD90, ms)), patch clamp screening, voltage clamp screening and concentration response assays.

For example, where the sensitivity of a CaSR is to be determined in a cell, stimulus-evoked changes in intracellular calcium, e.g., those evoked by the presence of a candidate calcimimetic drug, may be used to determine calcium sensitivity. For example, assays for the release of calcium from internal stores, which can be monitored at the single-cell level using calcium-indicator dyes, are well known. (Chandrashekar et al., Cell 100:703-711 (2000); Nelson et al., Cell 106:381-390 (2001); Tsien et al., Cell Calcium 6:145-157 (1985)).

Further, intracellular free calcium levels prior to and after exposure of a CaSR (either naturally present or recombinantly expressed in a cell) to a candidate calcimimetic drug may be measured to determine if and to what degree the serum ionized calcium concentration, and accordingly, the calcium sensitivity of CaSR, is affected by a candidate calcimimetic drug. For example, intracellular free calcium concentration can be measured by microspectrofluorometry using the fluorescent indicator dye Fura-2/AM (Bush et al., J. Neurochem. 57, 562-74, 1991). Stably transfected cells are seeded onto a culture dish containing a glass coverslip insert. Cells are washed with HBS, incubated with a test compound, and loaded with Fura-2/AM (10 μM) for 20-40 minutes. After washing with HBS to remove the Fura-2/AM solution, cells are equilibrated in HBS for 10-20 minutes. Cells are then visualized under the 40.times. objective of a Leitz Fluovert FS microscope. Fluorescence emission is determined at 510 nM, with excitation wavelengths alternating between 340 nM and 380 mM. Raw fluorescence data are converted to calcium concentrations using standard calcium concentration curves and software analysis techniques.

Such assays are well-known to one of skill in the art and, based on the present description, may be adapted to the methods of the present invention with no more than routine experimentation. Assays may be modified to accommodate automation of the assay and may be accomplished in any vessel suitable for containing the reactants. Examples include microtitre plates, test tubes, and micro-centrifuge tubes.

In some embodiments, the candidate calcimimetic drugs to be assayed are selected from a library of compounds. These libraries may be generated using combinatorial synthetic methods.

Animal models expressing an CaSR allelic variant of interest or "altered CaSR" may be used as an in vivo assay for evaluating the efficacy of a candidate calcimimetic drug for hyperparathyroidism. For example, an altered CaSR may be expressed in Xenopus oocytes, e.g., introducing an RNA encoding a CaSR into Xenopus oocytes to transiently express the receptor. CaSR calcium sensitivity of altered CaSR in the Xenopus oocytes upon exposure to a candidate calcimimetic drug may be assessed by the assay methods described above.

Provided also are diagnostic kits comprising useful components for practicing the methods of the present invention. For example, a kit may comprise at least one of the primers needed for the PCR amplification, if PCR amplification is used, and also control DNA suitable for determining the success of the PCR reaction and/or to confirm the identification of the presence or absence of a polymorphism in a sample. A kit usually contains a matched pair of forward and reverse primers as described above for amplifying a segment encompassing a polymorphism of the present invention. For selective amplification of mutant or wildtype alleles, kits usually contain a pair of primers for amplification of the mutant allele and/or a separate pair of primers for amplification of the wildtype allele. Optional additional components of the kit include, for example, restriction enzymes for analysis of amplification products, reverse-transcriptase or polymerase, the substrate nucleoside triphosphates, and the appropriate buffers for reverse transcription, PCR, or restriction enzyme reactions.

A kit may also comprise reagents, buffers, controls and other compositions suitable for carrying out assays to assess the calcium sensitivity of a CaSR protein.

Usually, a kit also contains instructions for carrying out the methods. Kit components may be packaged for either manual or partially or wholly automated practice of the foregoing methods. Such kits may have a variety of uses, including, for example, diagnosis, therapy, and other applications.

EQUIVALENTS

The present invention provides, among other things, systems and methods for testing or predicting the efficacy of certain drugs in treating hyperparathyroidism. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

I claim:

1. A method of assessing efficacy of cinacalcet to treat secondary hyperparathyroidism in a human subject, comprising:
   determining which genotype for a single-nucleotide polymorphism site encoding amino acid residue 990 of a calcium-sensitive receptor (CaSR) gene the subject carries; and
   concluding that cinacalcet will have:
   a higher efficacy if the subject has a $^{990}$Gly-$^{990}$Gly or a $^{990}$Gly-$^{990}$Arg genotype; or
   a lower efficacy if the subject has a $^{990}$Arg-$^{990}$Arg genotype.

2. The method of claim 1, wherein the polymorphism site occurs at position 1 of codon 990 of the CaSR gene.

3. The method of claim 2, wherein the genotype is determined by amplifying nucleic acid of the subject that surrounds and includes the polymorphism site, sequencing the amplified nucleic acid, and identifying the subject as having:
   the $^{990}$Arg-$^{990}$Arg genotype if position 1 of codon 990 is sequenced as adenine; or
   the $^{990}$Gly-$^{990}$Gly genotype if position 1 of codon 990 is sequenced as guanine; or
   the $^{990}$Gly-$^{990}$Arg genotype if position 1 of codon 990 is sequenced as polymorphic for adenine and guanine.

4. The method of claim 3, wherein amplified nucleic acid is sequenced with a sense primer and with an antisense primer to cross-check the sequencing.

5. The method of claim 1, wherein the genotype is determined by performing in situ hybridization with a sequence-specific probe.

6. A method of predicting efficacy of cinacalcet to treat secondary hyperparathyroidism in a human subject, comprising:
   determining whether at least one calcium-sensitive receptor (CaSR) gene allele the subject carries encodes for glycine at amino acid residue 990 of the CaSR; and
   concluding that cinacalcet will have:
   a higher efficiency if the subject carries at least one CaSR allele encoding for glycine at amino acid residue 990 of the CaSR; or
   a lower efficacy if the subject does not carry at least one CaSR allele encoding for glycine at amino acid residue 990 of the CaSR.

7. The method of claim 6, wherein the genotype is determined by amplifying nucleic acid of the subject encoding amino acid residue 990 of the CaSR, sequencing the amplified nucleic acid, and identifying the subject as having:
   at least one CaSR allele encoding for glycine at amino acid residue 990 of the CaSR if position 1 of codon 990 is sequenced as guanine or polymorphic for adenine and guanine; or
   no CaSR allele encoding for glycine at amino acid residue 990 of the CaSR if position 1 of codon 990 is sequenced as adenine.

8. The method of claim 7, wherein amplified nucleic acid is sequenced with a sense primer and with an antisense primer to cross-check the sequencing.

9. The method of claim 6, wherein the genotype is determined by performing in situ hybridization with a sequence-specific probe.

* * * * *

UNITED STATES PATENT AND TRADEMARK OFFICE
CERTIFICATE OF CORRECTION

PATENT NO. : 7,595,161 B2 Page 1 of 1
APPLICATION NO. : 11/456712
DATED : September 29, 2009
INVENTOR(S) : Hansjoerg Martin Rothe It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 485 days.

Signed and Sealed this

Twenty-eighth Day of September, 2010

David J. Kappos
*Director of the United States Patent and Trademark Office*